United States Patent
Kropf et al.

(10) Patent No.: US 11,174,451 B2
(45) Date of Patent: Nov. 16, 2021

(54) ANIONIC SURFACTANTS AND DETERGENTS AND CLEANING AGENTS CONTAINING SAME

(71) Applicant: Henkel AG & Co. KGaA, Duesseldorf (DE)

(72) Inventors: Christian Kropf, Hilden (DE); Alexander Schulz, Essen (DE); Anna Klemmer, Duesseldorf (DE); Regina Palkovits, Aachen (DE); Peter Hausoul, GE Landgraaf (NL); Lukas Kipshagen, Aachen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 163 days.

(21) Appl. No.: 16/273,382

(22) Filed: Feb. 12, 2019

(65) Prior Publication Data
US 2019/0169531 A1    Jun. 6, 2019

Related U.S. Application Data

(63) Continuation of application No. PCT/EP2017/070090, filed on Aug. 8, 2017.

(30) Foreign Application Priority Data

Aug. 12, 2016 (DE) ............ 10 2016 009 798.1

(51) Int. Cl.
| | | |
|---|---|---|
| *C11D 1/00* | (2006.01) | |
| *C11D 1/26* | (2006.01) | |
| *C07D 307/12* | (2006.01) | |
| *C11D 17/04* | (2006.01) | |
| *B01J 29/70* | (2006.01) | |
| *B01J 29/03* | (2006.01) | |
| *B01J 29/08* | (2006.01) | |

(52) U.S. Cl.
CPC ............ *C11D 1/26* (2013.01); *C07D 307/12* (2013.01); *C11D 17/043* (2013.01); *C11D 17/044* (2013.01); *B01J 29/03* (2013.01); *B01J 29/084* (2013.01); *B01J 29/7007* (2013.01)

(58) Field of Classification Search
CPC ............ C11D 3/32; C11D 3/30; C11D 3/91
See application file for complete search history.

(56) References Cited

U.S. PATENT DOCUMENTS

| | | | |
|---|---|---|---|
| 3,855,248 A | 12/1974 | Lannert et al. | |
| 3,923,679 A | 12/1975 | Rapko | |
| 4,013,579 A | 3/1977 | Nakasone et al. | |
| 2017/0369816 A1* | 12/2017 | Holland | C11D 1/75 |

FOREIGN PATENT DOCUMENTS

| | | |
|---|---|---|
| CN | 103073526 A | 5/2013 |
| GB | 1320178 A | 6/1973 |
| WO | 2015094970 A1 | 6/2015 |

OTHER PUBLICATIONS

PCT International Search Report PCT/EP2017/070090 Completed: Nov. 15, 2017; dated Nov. 24, 2017 2 pages.

* cited by examiner

*Primary Examiner* — Necholus Ogden, Jr.
(74) *Attorney, Agent, or Firm* — Thomas G. Krivulka

(57) ABSTRACT

An anionic surfactant of general formula (I) in which n and m are, independently of one another, numbers from 0 to 17 and $2<n+m<20$, and $X^+$ is a charge-balancing cation. The invention also relates to a production method by way of: the acid-catalysed reaction of 2,5-bis(hydroxymethyl) tetrahydrofuran with an alkene having 5 to 22 C atoms in equimolar amounts, at an increased temperature; subsequent sulphation with a sulphating agent; and optional neutralisation by a subsequent reaction with

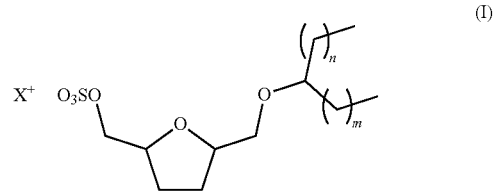

(I)

$X^+OH^-$ or $X^+_2 CO^{2-}_3$, where $X^+$ is an alkali metal cation or a group $N^+R^1R^2R^3$, in which $R^1$, $R^2$ and $R^3$ are, independently of one another, hydrogen, an alkyl group with 1 to 6 C atoms, or a hydroxyalkyl group with 2 to 6 C atoms. Detergents or cleaning agents containing—the surfactant, and the use of same to improve the performance of the detergents or cleaning agents, are also disclosed.

7 Claims, No Drawings

ANIONIC SURFACTANTS AND DETERGENTS AND CLEANING AGENTS CONTAINING SAME

FIELD OF THE INVENTION

The invention relates to anionic surfactants which can be prepared on the basis of renewable raw materials and which have low critical micelle concentrations (CMC) and produce low interfacial tensions. The invention also relates to a method for preparing surfactants of this kind and to washing or cleaning agents containing these surfactants.

BACKGROUND OF THE INVENTION

The use of surfactants to reduce the surface tension of water, to form dispersions and to solubilize has been generally known in the field of washing and cleaning agents for a long time. Although many surfactants are prepared wholly or in part on the basis of renewable raw materials, some powerful and widely used representatives are still based on petrochemicals. In addition, there is a constant desire to provide surfactants having outstanding practical properties in order to achieve high performance even with low surfactant use.

BRIEF SUMMARY OF THE INVENTION

The object of the present invention is to provide surfactants which have advantageous practical properties, such as a low CMC afifnd a low surface tension, and can be produced on the basis of renewable raw materials. In addition, the surfactants should be well-tolerated by the skin and it should also be possible to formulate said surfactants together with other surfactants so that they are particularly suitable for use in washing and cleaning agents.

In a first embodiment, the subject matter of the present invention is an anionic surfactant of general formula (I),

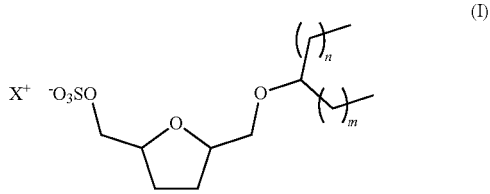

in which n and m independently of one another represent numbers from 0 to 17, preferably n represents a number from 0 to 3 and m represents a number from 5 to 14, and 2<n+m<20, preferably 6<n+m<16, and $X^+$ represents a charge-balancing cation. $X^+$ is preferably selected from the group comprising the proton, alkali metal cations and the group $N^+R^1R^2R^3$, in which $R^1$, $R^2$ and $R^3$ independently of one another represent hydrogen, an alkyl group having 1 to 6 C atoms or a hydroxy alkyl group having 2 to 6 C atoms.

Surfactants of general formula (I) can be prepared by sulfating a compound of general formula (II),

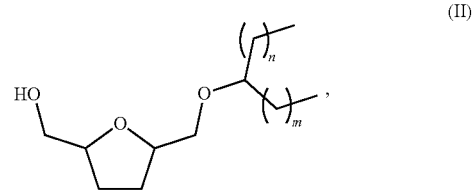

in which n and m have the meanings stated above, using a sulfating agent, for example chlorosulfonic acid or sulfur trioxide pyridine, and optionally neutralizing by subsequent reaction with $X^+OH^-$, where $X^+$ has the meanings stated above. Compounds of general formula (II) can be obtained by monoalkylation of 2,5-bis(hydroxymethyl) tetrahydrofuran, in particular by the reaction thereof with alkenes. 2,5-bis(hydroxymethyl) tetrahydrofuran can be obtained by hydrogenation of hydroxymethylfurfural, an intermediate from the conversion of cellulose. n and m, in particular when alkene mixtures are used in the preparation of the surfactants according to the invention, can also assume non-integer values as sizes to be determined analytically.

Another object of the invention is a method for preparing a compound of general formula (I) defined above by acid-catalyzed reaction of 2,5-bis(hydroxymethyl) tetrahydrofuran with an alkene, in particular a 1-alkene, with 5 to 22, in particular 9 to 19 C atoms in equimolar amounts at elevated temperature, preferably at temperatures in the range of from 140° C. to 200° C., preferably under solvent-free conditions and preferably as thoroughly mixed as possible, to form a compound of general formula (II), subsequent sulfation using a sulfating agent and optionally neutralizing by means of subsequent reaction with $X^+OH^-$ or $X^+{}_2CO^{2-}{}_3$, where $X^+$ represents an alkali metal cation or a group $N^+R^1R^2R^3$, in which $R^1$, $R^2$ and $R^3$ independently of one another represent hydrogen, an alkyl group having 1 to 6 C atoms or a hydroxy alkyl group having 2 to 6 C atoms.

The surfactants according to the invention have very low CMC values and lead to very low interfacial tensions with respect to oil together with fast dynamics in the organization at the interface. Particularly preferred surfactants according to the invention have a CMC of from 0.01 g/l to 0.25 g/l in water at pH 8.5 and 25° C. and produce an interfacial tension at a concentration of 1 g/l in water at pH 8.5 and 25° C. of less than 8 mN/m which can be determined against isopropyl myristate by means of the spinning drop method (20 minutes equilibration time).

As explained, the surfactants according to the invention can be obtained from renewable raw materials. Said surfactants also have the advantage that the renewable raw materials from which they can be prepared do not provide a basis for the production of food, meaning that the food competition situation observed in some surfactants obtainable from other renewable raw materials does not exist in this case.

The surfactants according to the invention are preferably prepared by stirring 2,5-bis(hydroxymethyl) tetrahydrofuran together with the alkene and an acidic catalyst, in particular an acidic solid catalyst, for example an acidic zeolite or a zeolite in the so-called H-form, in particular zeolite beta and/or zeolite Y, at a temperature in the range of from 140° C. to 200° C., in particular from 180° C. to 200° C., for a period of 8 hours to 24 hours, in particular 12 hours to 18 hours, and a thorough as possible mixing of the reactants and the catalyst being particularly preferred. In order to process the resulting compound of general formula (II), the catalyst can be separated, preferably by centrifugation or filtration.

The reaction mixture can be separated, for example by distillation, and, in addition to the desired product, if desired, the unreacted starting materials can also be recovered. A resulting compound of general formula (II) is reacted with a sulfating agent, for example chlorosulfonic acid or sulfur trioxide pyridine, at a temperature in the range of preferably from −20° C. to 75° C., in particular from 25° C. to 75° C., and a duration of preferably 1 hour to 24 hours, in particular 6 to 18 hours. The charge-balancing cation present following the sulfation may then, if desired, be exchanged by reaction with $X^+OH^-$, for example 1M methanolic sodium hydroxide solution, or by reaction with $X^+_2CO^{2-}_3$, for example sodium carbonate. The surfactant of general formula (I) can be isolated, for example, by precipitation upon the addition of a suitable precipitating agent, in particular acetone, diethyl ether or petroleum ether.

The surfactants according to the invention are exceptionally suitable as an ingredient in washing and cleaning agents, cosmetics such as shampoos, toothpastes, and for the other fields of use in which anionic surfactants are currently conventionally used, for example in the food industry, geosciences, tertiary oil production, plastics engineering, metalworking, photography, paper recycling, tool cleaning, and fire fighting.

Particularly good results are achieved in the use of said surfactants in washing and cleaning agents, such that further subject matter of the present invention includes the use of anionic surfactant of general formula (I) for the preparation of washing or cleaning agents, the use of an anionic surfactant of general formula (I) for improving the performance of washing or cleaning agents in washing laundry or cleaning hard surfaces, and washing or cleaning agents containing a surfactant of general formula (I).

DETAILED DESCRIPTION OF THE INVENTION

An agent according to the invention preferably contains from 1 wt. % to 99 wt. %, in particular from 3 wt. % to 85 wt. %, and particularly preferably from 5 wt. % to 65 wt. %, of the surfactant of general formula (I).

In addition to the anionic surfactant of general formula (I), the washing or cleaning agent may contain further ingredients which further improve the practical and/or aesthetic properties of the agent. In the context of the present invention, the agent preferably additionally contains one or more substances from the group of non-ionic surfactants, anionic surfactants, builders, bleaching agents, bleach activators, enzymes, electrolytes, pH adjusters, perfumes, perfume carriers, fluorescing agents, dyes, hydrotopes, foam inhibitors, anti-redeposition agents, graying inhibitors, anti-shrink agents, anti-crease agents, dye transfer inhibitors, antimicrobial active ingredients, non-aqueous solvents, germicides, fungicides, antioxidants, preservatives, corrosion inhibitors, antistatic agents, bittering agents, ironing aids, repellents and impregnating agents, skincare active ingredients, anti-swelling and anti-slip agents, softening components, and UV absorbers.

An agent according to the invention preferably contains, in addition to the anionic surfactant of general formula (I), up to 99 wt. %, in particular from 3 wt. % to 85 wt. %, and particularly preferably from 5 wt. % to 65 wt. %, of a further surfactant, the additionally present surfactants preferably also being obtainable from renewable raw materials.

The agent according to the invention may contain non-ionic surfactants. Suitable non-ionic surfactants include alkoxylated fatty alcohols, alkoxylated fatty acid alkyl esters, fatty acid amides, alkoxylated fatty acid amides, polyhydroxy fatty acid amides, alkylphenol polyglycol ethers, amine oxides, alkyl polyglucosides and mixtures thereof.

Alkoxylated fatty alcohols that are preferably used are ethoxylated, in particular primary, alcohols having preferably 8 to 18 C atoms and, on average, 4 to 12 mol of ethylene oxide (EO) per mol of alcohol, in which the alcohol functional group is linear. Alcohol ethoxylates having 12 to 18 C atoms, for example of coconut, palm, tallow fatty or oleyl alcohol, and an average of 5 to 8 EO per mole of alcohol are particularly preferred. Examples of preferred ethoxylated alcohols are $C_{12-14}$ alcohols having 4 EO or 7 EO, $C_{9-11}$ alcohol having 7 EO, $C_{12-18}$ alcohols having 5 EO or 7 EO, and mixtures thereof. The degrees of ethoxylation indicated represent statistical averages that can correspond to an integer or a fractional number for a specific product. Preferred alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO. Non-ionic surfactants that contain EO and PO groups together in the molecule can also be used according to the invention. Furthermore, a mixture of a (more highly) branched ethoxylated fatty alcohol and an unbranched ethoxylated fatty alcohol, such as a mixture of a $C_{16-18}$ fatty alcohol with 7 EO and 2-propylheptanol with 7 EO, are also suitable. The amount of nonionic surfactant is preferably up to 25 wt. %, in particular 1 wt. % to 20 wt. %, the wt. % stated here and in the following in each case being based on the total washing agent, unless stated otherwise.

Optional additional anionic surfactants include alkylbenzene sulfonic acid salts, olefin sulfonic acid salts, $C_{12-18}$ alkane sulfonic acid salts, salts of sulfuric acid monoesters having a fatty alcohol, fatty acid soaps, salts of sulfuric acid monoesters having an ethoxylated fatty alcohol, or a mixture of two or more of these anionic surfactants.

Surfactants of the sulfonate type that can be used are, for example, $C_{9-13}$ alkylbenzene sulfonates, olefin sulfonates, that is to say mixtures of alkene and hydroxy alkane sulfonates, and disulfonates, as obtained, for example, from $C_{12-18}$ monoolefins having a terminal or internal double bond by way of sulfonation with gaseous sulfur trioxide and subsequent alkaline or acid hydrolysis of the sulfonation products. $C_{12-18}$ alkane sulfonates and the esters of α-sulfofatty acids (ester sulfonates) are suitable, for example the α-sulfonated methyl esters of hydrogenated coconut fatty acids, palm kernel fatty acids or tallow fatty acids.

The salts of the sulfuric acid half-esters of $C_{12}$-$C_{18}$ fatty alcohols, for example from coconut fatty alcohol, tallow fatty alcohol, lauryl alcohol, myristyl alcohol, cetyl alcohol or stearyl alcohol, or of $C_{10}$-$C_{20}$ oxo alcohols and those half-esters of secondary alcohols having this chain length are preferred as alk(en)yl sulfates. From a washing perspective, the $C_{12}$-$C_{16}$ alkyl sulfates, $C_{12}$-$C_{15}$ alkyl sulfates and $C_{14}$-$C_{15}$ alkyl sulfates are preferred.

Fatty alcohol ether sulfates, such as the sulfuric acid monoesters of straight-chain or branched $C_{7-21}$ alcohols ethoxylated with 1 to 6 mol of ethylene oxide, such as 2-methyl-branched $C_{9-11}$ alcohols having, on average, 3.5 mol ethylene oxide (EO) or $C_{12-18}$ fatty alcohols having 1 to 4 EO, are also suitable.

Further suitable anionic surfactants are fatty acid soaps. Saturated and unsaturated fatty acid soaps are suitable, such as the salts of lauric acid, myristic acid, palmitic acid, stearic acid, (hydrogenated) erucic acid and behenic acid, and in particular soap mixtures derived from natural fatty acids, such as coconut, palm kernel, olive oil or tallow fatty acids.

The additional anionic surfactants, including the fatty acid soaps, may be present in the form of the sodium, potassium or magnesium or ammonium salts thereof. The anionic surfactants are preferably present in the form of the sodium or ammonium salts thereof. Amines which can be used for neutralization are preferably choline, triethylamine, monoethanolamine, diethanolamine, triethanolamine, methylethylamine or a mixture thereof, with monoethanolamine being preferred. In a particularly preferred embodiment, the agent, in particular when in liquid form, contains monoethanolamine-neutralized alkylbenzene sulfonic acid, in particular $C_{9-13}$ alkylbenzene sulfonic acid, and/or monoethanolamine-neutralized fatty acid.

The content of additional anionic surfactant, if any, in the agent according to the invention is preferably up to 30 wt. %, in particular 1 wt. % to 25 wt. %.

An agent according to the invention preferably contains at least one water-soluble and/or water-insoluble, organic and/or inorganic builder. The water-soluble organic builders include polycarboxylic acids, in particular citric acid and saccharic acids, monomeric and polymeric aminopolycarboxylic acids, in particular glycinediacetic acid, methylglycinediacetic acid, nitrilotriacetic acid, iminodisuccinates such as ethylenediamine N,N'-disuccinic acid and hydroxy iminodisuccinates, ethylenediaminetetraacetic acid and polyaspartic acid, polyphosphonic acids, in particular aminotris(methylene phosphonic acid), ethylenediamine tetrakis (methylenephosphonic acid), lysine tetra(methylene phosphonic acid) and 1-hydroxyethane-1,1-diphosphonic acid, polymeric hydroxy compounds such as dextrin, and polymeric (poly)carboxylic acids, in particular polycarboxylates that can be obtained from polysaccharides by oxidation, polymeric acrylic acids, methacrylic acids, maleic acids, and mixed polymers thereof, which may also contain small portions of polymerizable substances, without a carboxylic acid functionality, in the polymer. The relative average molecular weight of the homopolymers of unsaturated carboxylic acids is generally between 5,000 g/mol and 200,000 g/mol, that of the copolymers is between 2,000 g/mol and 200,000 g/mol, preferably 50,000 g/mol to 120,000 g/mol, in each case based on free acids. A particularly preferred acrylic acid-maleic acid copolymer has a relative average molecular weight of 50,000 to 100,000. Compounds of this class which are suitable, although less preferred, are copolymers of acrylic acid or methacrylic acid with vinyl ethers, such as vinyl methyl ethers, vinyl esters, ethylene, propylene, and styrene, in which the proportion of the acid is at least 50 wt. %. As water-soluble organic builders it is also possible to use terpolymers containing as monomers two unsaturated acids and/or salts thereof and, as third monomer, vinyl alcohol and/or a vinyl alcohol derivative or a carbohydrate. The first acidic monomer or the salt thereof is derived from a monoethylenically unsaturated $C_3$-$C_8$ carboxylic acid and preferably from a $C_3$-$C_4$ monocarboxylic acid, in particular from (meth)acrylic acid. The second acidic monomer or the salt thereof may be a derivative of a $C_4$-$C_8$ dicarboxylic acid, with maleic acid being particularly preferred. The third monomeric unit is formed in this case of vinyl alcohol and/or preferably an esterified vinyl alcohol. Particularly preferred are vinyl alcohol derivatives which are an ester of short-chain carboxylic acids, for example $C_1$-$C_4$ carboxylic acids, with vinyl alcohol. Preferred polymers contain from 60 wt. % to 95 wt. %, in particular from 70 wt. % to 90 wt. %, of (meth)acrylic acid or (meth)acrylate, particularly preferably acrylic acid or acrylate, and maleic acid or maleate and 5 wt. % to 40 wt. %, preferably 10 wt. % to 30 wt. % of vinyl alcohol and/or vinyl acetate. Very particular preference is given to polymers in which the weight ratio of (meth)acrylic acid or (meth)acrylate to maleic acid or maleate is between 1:1 and 4:1, preferably between 2:1 and 3:1 and in particular 2:1 and 2.5:1. The amounts and the weight ratios are based on the acids. The second acidic monomer or the salt thereof may also be a derivative of an allylsulfonic acid which is substituted in the 2nd position by an alkyl functional group, preferably by a $C_1$-$C_4$ alkyl functional group, or an aromatic functional group which is preferably derived from benzene or benzene derivatives. Preferred terpolymers contain from 40 wt. % to 60 wt. %, in particular from 45 wt. % to 55 wt. % (meth)acrylic acid or (meth)acrylate, particularly preferably acrylic acid or acrylate, from 10 wt. % to 30 wt. %, preferably 15 wt. % to 25 wt. % methallyl sulfonic acid or methallyl sulfonate and as the third monomer 15 wt. % to 40 wt. %, preferably 20 wt. % to 40 wt. % of a carbohydrate. This carbohydrate may be, for example, a mono-, di-, oligo- or polysaccharide, mono-, di- or oligosaccharides being preferred. Sucrose is particularly preferred. The use of the third monomer presumably incorporates predetermined breaking points into the polymer which are responsible for the good biodegradability of the polymer. These terpolymers generally have a relative average molecular weight of between 1,000 g/mol and 200,000 g/mol, preferably between 200 g/mol and 50,000 g/mol. Further preferred copolymers contain acrolein and acrylic acid/acrylic acid salts or vinyl acetate as monomers. The organic builders may, in particular for the preparation of liquid agents, be used in the form of aqueous solutions, preferably in the form of 30 to 50 wt. % aqueous solutions. All indicated acids are generally used in the form of water-soluble salts thereof, in particular alkali salts thereof.

Organic builders of this kind may, if desired, be contained in amounts of up to 40 wt. %, in particular up to 25 wt. %, and preferably from 1 wt. % to 8 wt. %. Amounts in the upper half of the stated ranges are preferably used in paste-form or liquid, in particular water-containing, agents.

In particular polyphosphates, preferably sodium triphosphate, are suitable as water-soluble inorganic builder materials. In particular crystalline or amorphous, water-dispersible alkali aluminosilicates are used as water-insoluble inorganic builder materials in amounts of no more than 25 wt. %, preferably of from 3 wt. % to 20 wt. % and in particular in amounts of from 5 wt. % to 15 wt. %. Among these, crystalline sodium aluminosilicates of washing agent quality, in particular zeolite A, zeolite P and zeolite MAP and optionally zeolite X, are preferred. Amounts close to the stated upper limit are preferably used in solid, particulate agents. Suitable aluminosilicates have in particular no particles having a particle size greater than 30 μm and preferably comprise at least 80 wt. % of particles having a size smaller than 10 μm. The calcium binding capacity thereof is generally in the range of from 100 to 200 mg CaO per gram.

In addition to or as an alternative to said water-insoluble aluminosilicate and alkali carbonate, further water-soluble inorganic builder materials may be contained. In addition to the polyphosphates, such as sodium triphosphate, these include in particular the water-soluble crystalline and/or amorphous alkali silicate builders. Water-soluble inorganic builder materials of this kind are contained in the agents in amounts of from 1 wt. % to 20 wt. %, in particular from 5 wt. % to 15 wt. %. The alkali silicates that are usable as builder materials preferably have a molar ratio of alkali oxide to $SiO_2$ of less than 0.95, in particular from 1:1.1 to 1:12, and may be present in amorphous or crystalline form. Preferred alkali silicates are sodium silicates, in particular amorphous sodium silicates having a Na$_2$O:SiO$_2$ molar ratio of from 1:2 to 1:2.8. Preferably used as crystalline silicates, which may be present alone or in a mixture with amorphous silicates, are crystalline phyllosilicates of general formula Na$_2$Si$_x$O$_{2x+1}$·y H$_2$O, in which x, referred to as the module, is a number from 1.9 to 4, y is a number from 0 to 20, and preferred values for x are 2, 3 or 4. Preferred crystalline phyllosilicates are those in which x in the stated general formula assumes the values 2 or 3. Both β- and δ-sodium disilicates (Na$_2$Si$_2$O$_5$·y H$_2$O) are particularly preferred. Practically water-free crystalline alkali silicates of the above general formula, in which x is a number from 1.9 to 2.1 and which are produced from amorphous alkali silicates, may also be used in the agents. In another preferred embodiment, a crystalline sodium phyllosilicate having a module of 2 to 3, which may be prepared from sand and soda, is used. Crystalline sodium silicates having a module in the range of from 1.9 to 3.5 are used in a further embodiment. In a preferred embodiment of agents of this kind, a granular compound of alkali silicate and alkali carbonate is used, as it is commercially available, for example, under the name Nabion® 15.

Suitable peroxidic bleaches are, in particular, organic peracids or peracid salts of organic acids, such as phthalimidopercaproic acid, perbenzoic acid, monoperoxyphthalic acid, and diperdodecanedioic acid and salts thereof, such as magnesium monoperoxyphthalate, diacyl peroxides, hydrogen peroxide and inorganic salts which release hydrogen peroxide under the conditions of use, such as alkali metal perborate, alkali metal percarbonate and/or alkali metal per silicate, and hydrogen peroxide inclusion compounds such as H$_2$O$_2$ urea adducts, and mixtures thereof. Hydrogen peroxide can also be produced by means of an enzymatic system, i.e. an oxidase and a substrate thereof. If solid peroxygen compounds are intended to be used, these may be used in the form of powders or granules, which may also be encased in a manner known in principle. Particular preference is given to using alkali metal percarbonate, alkali metal perborate monohydrate or hydrogen peroxide. A washing agent which can be used in the context of the invention contains peroxidic bleaching agent in amounts of preferably up to 60 wt. %, in particular from 5 wt. % 50 wt. % and particularly preferably from 15 wt. % to 30 wt. % or, alternatively, from 2.5 wt. % to 20 wt. %, with hydrogen peroxide being the particularly preferred peroxidic bleaching agent in liquid agents and sodium percarbonate in solid agents. Preferably, peroxidic bleaching agent particles have a particle size in the range of from 10 μm to 5000 μm, in particular from 50 μm to 1000 μm and/or a density of from 0.85 g/cm$^3$ to 4.9 g/cm$^3$, in particular from 0.91 g/cm$^3$ to 2.7 g/cm$^3$.

In particular, compounds that, under perhydrolysis conditions, result in optionally substituted perbenzoic acid and/or aliphatic peroxycarboxylic acids having 1 to 12 C atoms, in particular 2 to 4 C atoms, either in isolation or in mixtures, can be used as a bleach-activating compound that provides peroxycarboxylic acid under perhydrolysis conditions. Bleach activators that bear O acyl and/or N acyl groups, particularly of the stated number of C atoms, and/or optionally substituted benzoyl groups, are suitable. Preferred are polyacylated alkylene diamines, in particular tetraacetylethylenediamine (TAED), acylated glycolurils, in particular tetraacetylglycoluril (TAGU), acylated triazine derivatives, in particular 1,5-diacetyl-2,4-dioxohexahydro-1,3,5-triazine (DADHT), N-acylimides, in particular N-nonanoyl succinimide (NOSI), acylated phenol sulfonates or phenol carboxylates or the sulfonic or carboxylic acids thereof, in particular nonanoyl or isononanoyl or lauroyloxy benzenesulfonate (NOBS, iso-NOBS or LOBS, respectively), or decanoyl oxybenzoate (DOBA), the formal carbonic acid ester derivatives thereof such as 4(-2-decanoloxy ethoxycarbonyloxy) benzene sulfonate (DECOBS), acylated polyhydric alcohols, in particular triacetin, ethylene glycol diacetate and 2,5-diacetoxy-2,5-dihydrofuran and acetylated sorbitol and mannitol and mixtures thereof (SORMAN), acylated sugar derivatives, in particular pentaacetyl glucose (PAG), pentaacetyl fructose, tetraacetyl xylose and octaacetyl lactose, and acetylated, optionally N-alkylated glucamine and gluconolactone, and/or N-acylated lactams, for example benzoyl caprolactam.

In addition to, or in place of, compounds which form peroxycarboxylic acids under perhydrolysis conditions, other bleach-activating compounds, for example nitriles, from which perimidic acids may form under perhydrolysis conditions, may be present. These include in particular aminoacetonitrile derivatives having quaternized nitrogen atom according to the formula

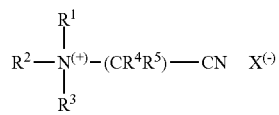

in which R$^1$ represents —H, —CH$_3$, a C$_{2\text{-}24}$ alkyl or alkenyl functional group, a substituted C$_{1\text{-}24}$ alkyl or C$_{2\text{-}24}$ alkenyl functional group having at least one substituent from the group —Cl, —Br, —OH, —NH$_2$, —CN and —N$^{(+)}$—CH$_2$—CN, an alkyl or alkenylaryl functional group having a C$_{1\text{-}24}$ alkyl group or represents a substituted alkyl or alkenylaryl functional group having at least one, preferably two, optionally substituted C$_{1\text{-}24}$ alkyl group(s) and optionally further substituents on the aromatic ring, R$^2$ and R$^3$ are independently selected from —CH$_2$—CN, —CH$_3$, —CH$_2$—CH$_3$, CH$_2$—CH$_2$—CH$_3$, —CH(CH$_3$)—CH$_3$, —CH$_2$—OH, —CH$_2$—CH$_2$—OH, —CH(OH)—CH$_3$, —CH$_2$—CH$_2$—CH$_2$—OH, —CH$_2$—CH(OH)—CH$_3$, —CH(OH)—CH$_2$—CH$_3$, —(CH$_2$CH$_2$—O)$_n$H where n=1, 2, 3, 4, 5 or 6, R$^4$ and R$^5$ independently of one another have a meaning stated above for R$^1$, R$^2$ or R$^3$, where at least 2 of the functional groups mentioned, in particular R$^2$ and R$^3$, can also be linked together to form a ring enclosing the nitrogen atom and optionally further heteroatoms and then preferably form a morpholino ring, and X is a charge-balancing anion, preferably selected from benzenesulfonate, toluenesulfonate, cumene sulfonate, the C$_{9\text{-}15}$ alkylbenzene-sulfonates, the C$_{1\text{-}20}$ alkyl sulfates, the C$_{8\text{-}22}$ carboxylic acid methyl ester sulfonates, sulfate, hydrogen sulfate and mixtures thereof, can be used. Bleach activators that form peroxycarboxylic acids or perimidic acids under perhydrolysis conditions are preferably present in agents according to the invention in amounts of up to 25 wt. %, in particular 0.1 wt. % to 10 wt. %. Preferably, bleaching agent particles have a particle size in the range of from 10 μm to 5000 μm, in particular from 50 μm to 1000 μm and/or a density of from 0.85 g/cm$^3$ to 4.9 g/cm$^3$, in particular from 0.91 g/cm$^3$ to 2.7 g/cm$^3$.

The presence of bleach-catalyzing transition metal complexes, in addition to or in place of said bleach activators, is possible. These are preferably selected from the cobalt, iron, copper, titanium, vanadium, manganese and ruthenium complexes. Suitable ligands in transition metal complexes of this kind are inorganic and organic compounds, which, in addition to carboxylates, include in particular compounds having primary, secondary and/or tertiary amine and/or alcohol functions, such as pyridine, pyridazine, pyrimidine, pyrazine, imidazole, pyrazole, triazole, 2,2'-bispyridylamine, tris(2-pyridylmethyl)amine, 1,4,7-triazacyclononane, 1,4,7-trimethyl-1,4,7-triazacyclononane, 1,5,9-trimethyl-1,5,9-triazacyclododecane, (bis((1-methylimidazol-2-yl)methyl))-(2-pyridylmethyl)-amine, N,N'-(bis(1-methylimidazole-2-yl)methyl)-ethylenediamine, N-bis(2-benzimidazolylmethyl)aminoethanol, 2,6-bis(bis(2-benzimidazolylmethyl)aminomethyl)-4-methylphenol, N,N,N',N'-tetrakis(2-benzimidazolylmethyl)-2-hydroxy-1,3-diaminopropane, 2,6-bis(bis(2-pyridylmethyl)aminomethyl)-4-methylphenol, 1,3-bis(bis-(2-benzimidazolylmethyl)aminomethyl) benzene, sorbitol, mannitol, erythritol, adonitol, inositol, lactose, and optionally substituted salens, porphins and porphyrins. The inorganic neutral ligands include in particular ammonia and water. If not all coordination sites of the transition metal central atom are occupied by neutral ligands, the complex contains further, preferably anionic, and among these in particular mono- or bidentate ligands. These include in particular the halides such as fluoride, chloride, bromide and iodide, and the $(NO_2)^-$ group, that is to say, a nitro ligand or a nitrito ligand. The $(NO_2)^-$ group may also be chelated to a transition metal or it may asymmetrically or μ1-O-bridge two transition metal atoms. In addition to the ligands mentioned, the transition metal complexes may bear further, generally simpler ligands, in particular mono- or polyvalent anion ligands. Nitrate, acetate, trifluoroacetate, formate, carbonate, citrate, oxalate, perchlorate and complex anions such as hexafluorophosphate are used, for example. The anion ligands should provide charge balance between the transition-metal central atom and the ligand system. The presence of oxo ligands, peroxo ligands and imino ligands is also possible. In particular, ligands of this kind can also act in a bridging manner, such that polynuclear complexes are produced. In the case of bridged, dinuclear complexes, it is not necessary for the two metal atoms in the complex to be the same. The use of binuclear complexes in which the two transition metal central atoms have different oxidation numbers is also possible. If anionic ligands are not present or the presence of anionic ligands does not result in charge balance in the complex, anionic counterions which neutralize the cationic transition metal complex are present in the transition metal complex compounds to be used according to the invention. These anionic counterions include in particular nitrate, hydroxide, hexafluorophosphate, sulfate, chlorate, perchlorate, the halides such as chloride or the anions of carboxylic acids such as formate, acetate, oxalate, benzoate or citrate. Examples of transition metal complex compounds that can be used are [N,N'-bis[(2-hydroxy-5-vinylphenyl)methylene]-1,2-diamino-cyclohexane]-manganese (III) chloride, [N,N'-bis[(2-hydroxy-5-nitrophenyl)methylene]-1,2-diamino-cyclohexane]-manganese (III) acetate, [N,N'-bis[(2-hydroxyphenyl)methylene]-1,2-phenylenediamine]-manganese (III) acetate, [N,N'-bis[(2-hydroxyphenyl)methylene]-1,2-diaminocyclohexane]-manganese (III) chloride, [N,N'-bis[(2-hydroxyphenyl)methylene]-1,2-diaminoethane]-manganese (III) chloride, [N,N'-bis[(2-hydroxy-5-sulfonatophenyl)methylene]-1,2-diaminoethane]-manganese (III) chloride, manganese oxalato complexes, nitropentammine cobalt (III) chloride, nitrite pentammine cobalt (III) chloride, hexammine cobalt (III) chloride, chloropentammine cobalt (III)-chloride and the peroxo complex $[(NH_3)_5Co—O—O—Co(NH_3)_5]Cl_4$.

Suitable as enzymes that can be used in the agents are those from the class of proteases, amylases, lipases, cutinases, pullulanases, hemicellulases, cellulases, oxidases, and peroxidases, and mixtures thereof. Enzymatic active ingredients obtained from fungi or bacteria, such as *Bacillus subtilis, Bacillus licheniformis, Bacillus lentus, Streptomyces griseus, Humicola lanuginosa, Humicola insolens, Pseudomonas pseudoalcaligenes, Pseudomonas cepacia* or *Coprinus* are particularly suitable. The enzymes may be adsorbed on carrier substances and/or embedded in casing substances to protect said enzymes from premature inactivation. Said enzymes are preferably contained in the washing or cleaning agents according to the invention in amounts of up to 5 wt. %, in particular from 0.002 wt. % to 4 wt. %. If the agent according to the invention contains protease, it preferably has a proteolytic activity in the range of approximately 100 PE/g to approximately 10,000 PE/g, in particular 300 PE/g to 8000 PE/g. If a plurality of enzymes are to be used in the agent according to the invention, this can be carried out by incorporating the two or more separate enzymes, or enzymes separately formulated in a known manner, or by two or more enzymes formulated together in a granulate.

For setting a desired pH that does not result from mixing the other components themselves, the agents according to the invention may contain acids that are compatible with the system and the environment, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium or alkali hydroxides. pH regulators of this kind are optionally contained in the agents according to the invention in amounts of preferably no greater than 20 wt. %, in particular from 1.2 wt. % to 17 wt. %.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides containing acidic groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethylcellulose, methylhydroxypropylcellulose, methylcarboxymethylcellulose and mixtures thereof, are preferably used, for example, in amounts of from 0.1 to 5 wt. %, based on the agents.

The agents may also contain, if desired, a conventional dye transfer inhibitor, preferably in amounts of up to 2 wt. %, in particular from 0.1 wt. % to 1 wt. %, which, in a preferred embodiment of the invention, is selected from polymers of vinylpyrrolidone, vinyl imidazole, vinyl pyridine-N-oxide, or the copolymers thereof. Polyvinylpyrrolidones having molecular weights of from 15,000 g/mol to 50,000 g/mol and also polyvinylpyrrolidones having higher molecular weights of, for example, up to more than 1,000,000 g/mol, in particular from 1,500,000 g/mol to 4,000,000 g/mol, N-vinylimidazole-N-vinylpyrrolidone copolymers, polyvinyloxazolidones, copolymers based on vinyl monomers and carboxamides, pyrrolidone group-containing polyesters and polyamides, grafted polyamidoamines and polyethyleneimines, polyamine-N-oxide polymers and polyvinyl alcohols may be used. However, it is also possible to use enzymatic systems comprising a peroxidase and hydrogen peroxide or a substance which provides hydrogen peroxide in water. The addition of a mediator compound for the peroxidase, for example an acetosyringone, a phenol derivative or a phenotiazine or phenoxazine, is preferred in this case, it being additionally possible to use above-mentioned polymeric dye transfer inhibitor active ingredients. Polyvinylpyrrolidone preferably has an average molar weight in the range of from 10,000 g/mol to 60,000 g/mol, in particular in the range of from 25,000 g/mol to 50,000 g/mol. Preferred copolymers are those from vinylpyrrolidone and vinylimidazole in a molar ratio of 5:1 to 1:1 having an average molar weight in the range of from 5,000 g/mol to 50,000 g/mol, in particular from 10,000 g/mol to 20,000 g/mol. However, in preferred embodiments of the invention, the washing agents are free of additional dye transfer inhibitors of this kind.

Washing agents may contain, for example, derivatives of diaminostilbene disulfonic acid or alkali metal salts thereof as optical brighteners, although said agents are preferably free of optical brighteners for use as color washing agents. Salts of 4,4'-bis(2-anilino-4-morpholino-1,3,5-triazinyl-6-amino)stilbene-2,2'-disulfonic acid or compounds having a similar structure which, instead of the morpholino group, bear a diethanolamino group, a methylamino group, an anilino group or a 2-methoxyethylamino group, are suitable, for example. Furthermore, brighteners of the substituted diphenol styryl type may also be present, for example the alkali salts of 4,4'-bis(2-sulfostyryl)diphenyl, 4,4'-bis(4-chloro-3-sulfostyryl)diphenyl, or 4-(4-chlorostyryl)-4'-(2-sulfostyryl)diphenyl. Mixtures of the aforementioned optical brighteners may also be used.

In particular, when used in mechanical processes, it may be advantageous to add conventional foam inhibitors to the agents. Soaps of natural or synthetic origin which have a high proportion of $C_{18}$-$C_{24}$ fatty acids are suitable as foam inhibitors, for example. Suitable non-surfactant-like foam inhibitors include, for example, organopolysiloxanes and mixtures thereof together with microfine, optionally silanated silicic acid and paraffins, waxes, microcrystalline waxes and mixtures thereof together with silanated silicic acid or bis-fatty acid alkylene diamides. Mixtures of various foam inhibitors are also advantageously used, for example those made up of silicones, paraffins, or waxes. The foam inhibitors, in particular silicone-containing and/or paraffin-containing foam inhibitors, are preferably bound to a granular carrier substance that is soluble or dispersible in water. Mixtures of paraffins and bistearylethylenediamide are particularly preferred.

In a preferred embodiment, the agent according to the invention is particulate and, in addition to the surfactant of general formula (I), contains builders, in particular in an amount in the range of from 1 wt. % 60 wt. %.

In another preferred embodiment, an agent according to the invention is liquid and contains from 1 wt. % to 90 wt. %, in particular from 10 wt. % to 85 wt. %, preferably from 25 wt. % to 75 wt. %, and particularly preferably from 35 wt. % to 65 wt. % water, water-miscible solvent or a mixture of water and water-miscible solvent. The water-miscible solvents include, for example, monohydric alcohols having 1 to 4 C atoms, in particular methanol, ethanol, isopropanol and tert-butanol, diols and triols having 2 to 4 C atoms, in particular ethylene glycol, propylene glycol and glycerol, and mixtures thereof, and the ethers that are derivable from the mentioned compound classes. Water-miscible solvents of this kind are preferably present in the agents according to the invention in amounts no greater than 30 wt. %, in particular from 2 wt. % to 20 wt. %.

In another preferred embodiment, the agent according to the invention is pre-portioned ready to be individually dosed in a chamber formed of water-soluble material and contains less than 15 wt. %, in particular in the range of from 1 wt. % to 12 wt. %, water. A portion is an independent dosing unit having at least one chamber in which the material to be dosed is contained. A chamber is a space delimited by walls (for example by a film), which can also exist without the material to be dosed (if necessary, by changing the shape thereof). A surface coating or a layer of a surface coating is thus not a wall according to the present invention.

The walls of the chamber are made of a water-soluble material. The water solubility of the material can be determined by means of a square film of said material (film: 22×22 mm with a thickness of 76 μm) fixed in a square frame (edge length on the inside: 20 mm) according to the following measurement protocol. Said framed film is immersed in 800 ml of distilled water kept at 20° C. in a 1 liter beaker with a circular bottom surface (Schott, Mainz, 1000 ml beaker, low form) such that the surface of the clamped film is arranged at right angles to the bottom surface of the beaker, the upper edge of the frame is 1 cm below the water surface and the lower edge of the frame is aligned in parallel with the bottom surface of the beaker in such a way that the lower edge of the frame extends along the radius of the bottom surface of the beaker and the center of the lower edge of the frame is arranged above the center of the radius of the beaker bottom. The material dissolves when stirred (stirring speed magnetic stirrer 300 rpm, stirring rod: 5 cm long) within 600 seconds in such a way that no single solid particles are visible to the naked eye.

The walls of the chambers and thus the water-soluble casings of the agents according to the invention are preferably formed by a water-soluble film material. Water-soluble packages of this kind can be made either by means of vertical fill-seal processes or thermoforming processes.

The thermoforming process generally includes forming a first layer of a water-soluble film material in order to form indentations for receiving a composition therein, filling the indentations with the composition, covering the composition-filled indentations with a second layer of a water-soluble film material, and sealing the first and second layers together at least around the protrusions.

The water-soluble film material is preferably selected from polymers or polymer mixtures. The casing may be made up of one or of two or more layers of water-soluble film material. The water-soluble film materials of the first layer and of the additional layers, if present, may be the same or different.

It is preferable for the water-soluble casing to contain polyvinyl alcohol or a polyvinyl alcohol copolymer; particularly preferably, it consists of polyvinyl alcohol or polyvinyl alcohol copolymer.

Water-soluble films for producing the water-soluble casing are preferably based on a polyvinyl alcohol or a polyvinyl alcohol copolymer of which the molecular weight is in the range of from 10,000 to 1,000,000 $gmol^{-1}$, preferably from 20,000 to 500,000 $gmol^{-1}$, particularly preferably from 30,000 to 100,000 $gmol^{-1}$ and in particular from 40,000 to 80,000 $gmol^{-1}$.

Polyvinyl alcohol is usually prepared by hydrolysis of polyvinyl acetate, since the direct synthesis route is not possible. The same applies to polyvinyl alcohol copolymers, which are produced accordingly from polyvinyl acetate copolymers. It is preferable for at least one layer of the water-soluble casing to include a polyvinyl alcohol of which the degree of hydrolysis is 70 to 100 mol. %, preferably 80 to 90 mol. %, particularly preferably 81 to 89 mol. %, and in particular 82 to 88 mol. %.

In addition, polymers selected from the group including acrylic acid-containing polymers, polyacrylamides, oxazoline polymers, polystyrene sulfonates, polyurethanes, polyesters, polyethers, polylactic acid and/or mixtures of said polymers may be added to a film material that is suitable for producing the water-soluble casing. Copolymerization of monomers underlying polymers of this kind, individually or in mixtures of two or more, with vinyl acetate is also possible.

In addition to vinyl alcohol, preferred polyvinyl alcohol copolymers include an ethylenically unsaturated carboxylic acid, or the salt or ester thereof. Polyvinyl alcohol copolymers of this kind particularly preferably contain, in addition to vinyl alcohol, acrylic acid, methacrylic acid, acrylic acid ester, methacrylic acid ester or mixtures thereof; preferred esters include $C_{1-4}$ alkyl ester or hydroxyalkyl ester. Likewise preferred polyvinyl alcohol copolymers include, in addition to vinyl alcohol, ethylenically unsaturated dicarboxylic acids as further monomers. Suitable dicarboxylic acids are, for example, itaconic acid, maleic acid, fumaric acid and mixtures thereof, with itaconic acid being particularly preferred.

Suitable water-soluble films for use in the casings of the water-soluble packages according to the invention are films which are sold by MonoSol LLC, for example under the designations M8630, C8400 or M8900. Other suitable films include films having the designations Solublon® PT, Solublon® GA, Solublon® KC or Solublon® KL from Aicello Chemical Europe GmbH, or the VF-HP films from Kuraray.

The washing or cleaning agent portion comprising the washing or cleaning agent and the water-soluble casing can comprise one or more chambers. The water-soluble casings comprising a chamber can have a substantially dimensionally stable spherical, rotationally ellipsoidal, cubic, cuboid or pillow-shaped design having a circular, elliptical, square or rectangular basic shape. The agent may be contained in one or more chambers, if present, of the water-soluble casing.

In a preferred embodiment, the water-soluble casing has two chambers. In this embodiment, the two chambers may each contain a solid sub-composition or each a liquid sub-composition, or the first chamber contains a liquid sub-composition and the second chamber a solid sub-composition.

The proportions of the agents contained in the different chambers of a water-soluble casing having two or more chambers may have the same composition. However, the agents in a water-soluble casing having at least two chambers preferably have sub-compositions which differ at least in one ingredient and/or in the content of at least one ingredient. Preferably, a sub-composition of agents of this kind according to the invention comprises enzyme and/or bleach activator and a further sub-composition separate therefrom comprises peroxidic bleaching agent, the first-mentioned sub-composition in particular having no peroxidic bleaching agent and the second-mentioned sub-composition in particular having no enzyme and no bleach activator.

By packaging into a water-soluble casing in portions, the user is able, for one application or, if desired, several, to put preferably one of the portions into the washing machine or dishwasher, in particular into the dispensing compartment of a washing machine, or in a container for carrying out a manual washing or cleaning process. Portion packets of this kind meet the consumer's desire for simplified dosing. After adding water, the casing material dissolves such that the ingredients are released and can be effective in the liquor. A portion that is encased so as to be water-soluble preferably weighs 10 g to 35 g, in particular 12 g to 28 g and particularly preferably 12 g to 15 g, where 0.3 g to 2.5 g, in particular 0.7 g to 1.2 g, accounts for the proportion of the water-soluble casing contained in the weight data.

The preparation of solid agents according to the invention poses no difficulties, and may take place in a known manner, for example by spray drying or granulation, with enzymes and potential further thermally sensitive ingredients, for example bleaching agents, being optionally added separately at a later stage. In order to prepare agents having an increased bulk weight, in particular in the range of from 650 g/l to 950 g/l, a method having an extrusion step is preferred.

Liquid or pasty agents according to the invention in the form of solutions containing water or conventional solvents are usually prepared by simply mixing the ingredients, which can be added in bulk or as a solution in an automatic mixer.

EXAMPLES

Example 1: Synthesis of sodium 5-[((dodecane-2-yloxy)methyl) tetrahydrofuran-2-yl]methylsulfate A: Preparation of 2,5-bis(hydroxymethyl) tetrahydrofuran (BHMTHF)

5.0 g of hydroxymethylfurfural (HMF; 40 mmol) was dissolved in 20 ml of ethanol and after addition of 0.25 g Ni/SiO$_2$ (5 wt. % based on HMF) stirred in an autoclave at a temperature of 100° C. and a pressure of 70 bar of hydrogen overnight. Following the reaction, the catalyst was separated by means of a syringe filter and the solvent was removed on a rotary evaporator. Distillation under reduced pressure gives the colorless product (3.5 g, 26.5 mmol, 70%).

$^1$H-NMR (400 MHz, CDCl$_3$): δ (ppm)=1.70 (m, 2H, H$_3$), 1.83 (m, 2H, H$_3$), 3.41 (dd, 2H, H$_1$), 3.65 (dd, 2H, H$_1$), 3.99 (m, 2H, H$_2$), 4.14 (s, 2H, OH).

$^{13}$C-NMR (100 MHz, CDCl$_3$): δ (ppm)=27.05 (s, 2C, C$_3$), 64.68 (s, 2C, C$_2$), 80.29 (s, 2C, C$_1$).

B: Preparation of 5-[((dodecane-2-yloxy)methyl) tetrahydrofuran-2-yl]methanol

A reaction mixture of 13.6 g of BHMTHF (103 mmol), 17.4 g of 1-dodecene (103 mmol) and 1.4 g of the catalyst zeolite H-BEA 15 was heated for 16 hours at 180° C. with maximum mixing. The mixture was then homogenized using 150 ml of isopropanol and the catalyst was separated off. Isopropanol was removed on the rotary evaporator and the residue extracted with methanol and petroleum ether. By distilling the petroleum ether fraction in a high vacuum, the remaining dodecene was separated at 60° C.; increasing the temperature to 120° C. provided 4.0 g of the product (13.4 mmol, 13%).

$^{13}$C-NMR (100 MHz, CDCl$_3$): δ (ppm)=14.24 (s, 1C, C$_{18}$), 19.51 (d, 1C, C$_7$), 22.81 (s, 1C, C$_{17}$), 25.61 (m, 1C, C$_{10}$), 27.73 (d, 1C, C$_3$), 28.34 (d, 1C, C$_4$), 29.75 (s, 3C, C$_{12-14}$), 29.81 (s, 1C, C$_{15}$), 29.89 (s, 1C, C$_{11}$), 32.04 (s, 1C, C$_{16}$), 36.45 (d, 1C, C$_9$), 65.82 (d, 1C, C$_1$), 70.61 (d, 1C, C$_6$), 78.38 (d, 1C, C$_8$), 79.04 (d, 1C, C$_5$), 80.20 (d, 1C, C$_2$).

C: Preparation of sodium 5-[((dodecane-2-yloxy) methyl) tetrahydrofuran-2-yl]methylsulfate 2.8 g of the branched BHMTHF ether (9.3 mmol) prepared in step B was dissolved in 5 ml of chloroform. Under ice-cooling, a solution of 1.1 g of chlorosulfonic acid (9.3 mmol) in 75 ml of chloroform was added dropwise over a period of 30 minutes. The ice-cooling is then withdrawn and the reaction mixture is stirred for 1 h at room temperature. The solvent was removed on the rotary evaporator and the residue dissolved in 5 ml methanol. The solution was neutralized using methanolic NaOH and a further 300 ml of methanol were added. The solid which formed during neutralization was separated off by means of a syringe filter. The solvent of the clear filtrate was removed on the rotary evaporator and the residue absorbed in a mixture of acetonitrile having little acetone. The desired product precipitated, was separated and dried. 1.3 g of sodium 5-[((dodecane-2-yloxy)methyl) tetrahydrofuran-2-yl]methyl sulfate (P1, 3.4 mmol, 40%) were obtained.

D: Alternative Preparation of Sodium 5-[((dodecane-2-yloxy)methyl)tetrahydrofuran-2-yl]methylsulfate 5.0 g of the branched BHMTHF ether (16.6 mmol) prepared in step B was dissolved in 200 ml of acetonenitrile. After adding 3.96 g of sulfur trioxide pyridine complex (24.9 mmol), the reaction mixture was heated to 75° C. and stirred for 6 hours. Following the reaction, 0.1 ml of fully desalinated water was added and the mixture was stirred at 75° C. for 10 minutes. Subsequently, the solvent was removed on the rotary evaporator and after drying the residue was received in 200 ml of ethanol in a high vacuum and mixed with 3.51 g of sodium carbonate (33.2 mmol). The mixture was stirred for two hours at 50° C. until gas evolution was no longer seen. The solution was then filtered by means of silica gel and said gel rinsed several times with ethanol. The liquid phases obtained were collected and the solvent removed on the rotary evaporator. After adding petroleum ether, a white solid precipitated which was mixed with petroleum ether after centrifugation and centrifuged again until the petroleum ether phase remained colorless after centrifugation. The resulting white product (P1, 3.8 g, 9.6 mmol, 58%) was dried on the rotary evaporator and dried in a high vacuum.

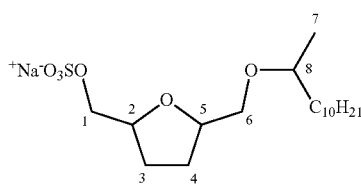

P1

$^{13}$C-NMR (100 MHz, D20): δ (ppm)=13.88 (s, 1C, C18), 19.14 (s, 1C, C17), 22.65 (s, 1C, C17), 25.58 (s, 1C, C10), 29.49 (s, 2C, C3,4), 29.84 (m, 5C, C11-15), 31.98 (s, 1C, C16), 36.22 (s, 1C, C9), 70.01 (s, 1C, C6), 71.14 (s, 1C, C1), 75.98 (s, 1C, C8), 77.55 (s, 1C, C2), 78.54 (s, 1C, C5).

The critical micelle concentration (CMC) of surfactant P1 was determined by measuring the surface tension of the aqueous solution thereof as a function of concentration at 25° C. and a pH of 8.5 to 0.11 g/l. The interfacial tension of an aqueous solution of P1 (concentration 1 g/l) with respect to isopropyl myristate at pH 8.5 and 25° C. was measured by means of the spinning drop method. After 20 minutes, the value was 4.2 mN/m.

Example 2: Synthesis of sodium 5-[((tetradecane-2-yloxy)methyl)tetrahydrofuran-2-yl]methyl sulfate (P2), sodium 5-[((hexadecan-2-yloxy)methyl)tetrahydrofuran-2-yl]methyl sulfate (P3) and sodium 5-[((octadecane-2-yloxy)methyl)tetrahydrofuran-2-yl]methyl sulfate (P4)

The surfactants P2 to P4 were prepared analogously to the method described in Example 1, although in step B, instead of the 1-dodecene, 1-tetradecene was used for P2, 1-hexadecene was used for P3 and 1-octadecene was used for P4.

The critical micelle concentration (CMC) of said surfactants was determined by measuring the surface tension of the respective aqueous solutions as a function of concentration at 25° C. and a pH of 8.5, and is set out in Table 1 below. The interfacial tension of an aqueous solution of the respective surfactants (concentration 1 g/l) with respect to isopropyl myristate at pH 8.5 and 25° C. was measured by means of the spinning drop method. After 20 minutes, the value stated in Table 1 below resulted.

TABLE 1

| Surfactant | CMC [g/l] | Interfacial tension [mN/m] |
|---|---|---|
| P2 | 0.02 | 3.2 |
| P3 | 0.004 | 1.7 |
| P4 | Not measurable | 0.6 |

Example 3: Washing Performance

The washing performance of P1 was tested in miniaturized form on the standardized stains on cotton set out in Table 2. At a washing temperature of 40° C., a washing time of 1 h and a dosage of 4.1 g/l of a washing agent V1, which was free of surfactants according to general formula (I), or a dosage of 4.1 g/l of a washing agent M1 which was otherwise composed as V1 but additionally contained 2 wt. % of surfactant P1, or a dosage of 4.1 g/liter of washing agent V2, which was otherwise composed as V1 but additionally contained 2 wt. % Na-dodecylbenzenesulfonate, as a result of colorimetric measurements, the differences in brightness values after and before washing (ΔΔY values) between the agents M1 and V1 and V2 and V1, likewise set out in Table 2, were obtained. Averages of 5-fold determinations are provided. The larger the value, the better the washing performance of M1 or V2 in comparison with V1.

TABLE 2

| Stain/Agent | M1 | V2 |
|---|---|---|
| Mayonnaise with soot | 1.4 | −0.2 |
| Used dripping | 1.3 | 1.0 |

What is claimed is:

1. A method for preparing an anionic surfactant, of general formula (I),

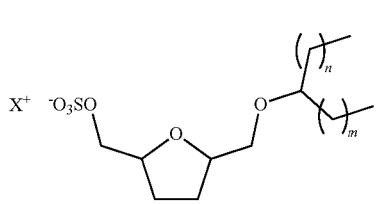
(I)

in which n and m independently of one another represent numbers from 0 to 17 and 2<n+m<20, and $X^+$ represents a charge-balancing cation, by acid-catalyzed reaction of 2,5-bis(hydroxymethyl) tetrahydrofuran with an alkene having C atoms in equimolar amounts at elevated temperature to form a compound of general formula (II),

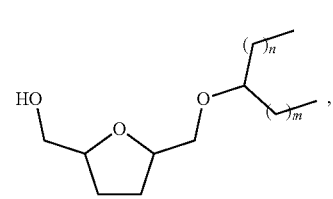
(II)

subsequent sulfation using a sulfating agent and optionally neutralizing by means of subsequent reaction with $X^+OH^-$ or $X^+_2 CO^{2-}_3$, where $X^+$ represents an alkali metal cation or a group $N^+R^1R^2R^3$, in which $R^1$, $R^2$ and $R^3$ independently of one another represent hydrogen, an alkyl group having 1 to 6 C atoms or a hydroxy alkyl group having 2 to 6 C atoms.

2. The method according to claim 1, characterized in that 2,5-bis (hydroxymethyl) tetrahydrofuran is stirred together with the alkene and an acidic catalyst at a temperature in the range from 140° C. to 200° C. for a period of 8 hours to 24 hours, and the resulting compound of general formula (II) is reacted with a sulfating agent at a temperature in the range from −20° C. to 75° C., and a duration of 1 hour to 24 hours.

3. The method according to claim 1, for preparing an anionic surfactant of general formula (I),

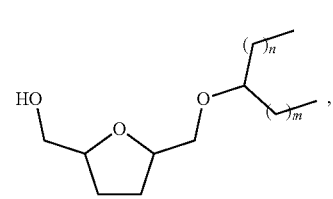
(I)

in which n and m independently of one another represent numbers from 0 to 17 and 2<n+m<20, and $X^+$ represents a charge-balancing cation, by acid-catalyzed reaction of 2,5-bis (hydroxymethyl) tetrahydrofuran with a 1-alkene, having 5 to 22 C atoms in equimolar amounts at elevated temperature to form a compound of general formula (II),

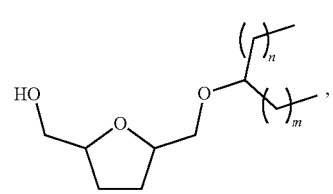
(II)

subsequent sulfation using a sulfating agent and optionally neutralizing by means of subsequent reaction with $X^+OH^-$ or $X^+_2 CO^{2-}_3$, where $X^+$ represents an alkali metal cation or a group $N^+R^1R^2R^3$, in which $R^1$, $R^2$ and $R^3$ independently of one another represent hydrogen, an alkyl group having 1 to 6 C atoms or a hydroxy alkyl group having 2 to 6 C atoms.

4. The method according to claim 1, for preparing an anionic surfactant of general formula (I),

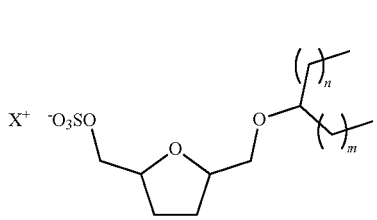
(I)

in which n and m independently of one another represent numbers from 0 to 17 and 2<n+m<20, and $X^+$ represents a charge-balancing cation, by acid-catalyzed reaction of 2,5-bis (hydroxymethyl) tetrahydrofuran with a 1-alkene, having 9 to 19 C atoms in equimolar amounts at elevated temperature to form a compound of general formula (II),

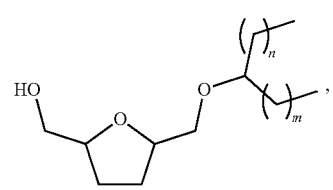
(II)

subsequent sulfation using a sulfating agent and optionally neutralizing by means of subsequent reaction with $X^+OH^-$ or $X^+_2 CO^{2-}_3$, where $X^+$ represents an alkali metal cation or a group $N^+R^1R^2R^3$, in which $R^1$, $R^2$ and $R^3$ independently of one another represent hydrogen, an alkyl group having 1 to 6 C atoms or a hydroxy alkyl group having 2 to 6 C atoms.

5. The method according to claim 2, characterized in that 2,5-bis (hydroxymethyl) tetrahydrofuran is stirred together with the alkene and an acidic solid catalyst at a temperature in the range from 180° C. to 200° C. for a period of 12 hours to 18 hours, and the resulting compound of general formula (II) is reacted with chlorosulfonic acid or sulfur trioxide pyridine at a temperature in the range from 25° C. to 75° C., and a duration of 6 to 18 hours.

6. The method according to claim 5, characterized in that the acidic solid catalyst is acidic zeolite or a zeolite in H-form.

7. The method according to claim 6, characterized in that the zeolite in H-form is zeolite beta and/or zeolite Y.

\* \* \* \* \*